US011534235B2

(12) United States Patent
Palushi et al.

(10) Patent No.: US 11,534,235 B2
(45) Date of Patent: Dec. 27, 2022

(54) NEEDLE INSTRUMENT FOR POSTERIOR NASAL NEURECTOMY ABLATION

(71) Applicants: Acclarent, Inc., Irvine, CA (US); Biosense Webster (Israel) Ltd., Yokneam (IL)

(72) Inventors: Jetmir Palushi, Irvine, CA (US); Fatemeh Akbarian, Rancho Palos Verdes, CA (US); Itzhak Fang, Irvine, CA (US); Athanasios Papadakis, Newport Beach, CA (US); Christopher T. Beeckler, Brea, CA (US); Julie M. Taylor, Yorba Linda, CA (US)

(73) Assignees: Acclarent, Inc., Irvine, CA (US); Biosense Webster (Israel) Ltd., Yokneam (IL)

(*) Notice: Subject to any disclaimer, the term of this patent is extended or adjusted under 35 U.S.C. 154(b) by 408 days.

(21) Appl. No.: 16/744,600

(22) Filed: Jan. 16, 2020

(65) Prior Publication Data
US 2020/0315697 A1    Oct. 8, 2020

Related U.S. Application Data

(60) Provisional application No. 62/829,068, filed on Apr. 4, 2019.

(51) Int. Cl.
*A61B 18/14* (2006.01)
*A61B 17/00* (2006.01)
(Continued)

(52) U.S. Cl.
CPC ............... *A61B 18/1477* (2013.01); *A61B 2017/00424* (2013.01); *A61B 2018/00077* (2013.01);
(Continued)

(58) Field of Classification Search
CPC ............ A61B 18/1477; A61B 18/1485; A61B 2017/00424; A61B 2018/00029;
(Continued)

(56) References Cited

U.S. PATENT DOCUMENTS 5,078,716 A    1/1992  Doll
5,336,222 A *  8/1994  Durgin, Jr .......... A61B 18/1477
                                               606/49
(Continued)

FOREIGN PATENT DOCUMENTS

CN    1222843 A    7/1999
CN    1224338 A    7/1999
(Continued)

OTHER PUBLICATIONS

Fukutake, Tomoshige, et al. "Laser surgery for allergic rhinitis." *Archives of Otolaryngology—Head & Neck Surgery* 112.12 (1986): 1280-1282.
(Continued)

*Primary Examiner* — Michael F Peffley
(74) *Attorney, Agent, or Firm* — Frost Brown Todd LLC

(57) ABSTRACT

A surgical instrument includes an outer tube configured to be gripped by a user, and a needle slidably disposed within the outer tube. The needle includes a needle lumen, a distal needle tip configured to pierce tissue, and an electrode disposed at the distal needle tip. The needle lumen opens to the distal needle tip such that the distal needle tip is configured to deliver fluid from the needle lumen to tissue. The electrode is operable to deliver RF energy to tissue for ablating the tissue. The needle is translatable relative to the outer tube between a proximal retracted position in which the distal needle tip is housed coaxially within the outer
(Continued)

tube, and a distal extended position in which the distal needle tip is exposed from the outer tube and configured to pierce tissue.

20 Claims, 10 Drawing Sheets

(51) Int. Cl.
A61B 18/00 (2006.01)
A61B 18/12 (2006.01)

(52) U.S. Cl.
CPC ............ *A61B 2018/00178* (2013.01); *A61B 2018/00327* (2013.01); *A61B 2018/00577* (2013.01); *A61B 2018/1253* (2013.01); *A61B 2218/002* (2013.01)

(58) Field of Classification Search
CPC .......... A61B 2018/00077; A61B 2018/00083; A61B 2018/00178; A61B 2018/00327; A61B 2018/00434; A61B 2018/00577; A61B 2018/00791; A61B 2018/00875; A61B 2018/1253; A61B 2018/1475; A61B 2218/002
See application file for complete search history.

(56) References Cited

U.S. PATENT DOCUMENTS

| | | | |
|---|---|---|---|
| 5,403,311 A * | 4/1995 | Abele | A61B 18/1492 606/49 |
| 5,514,131 A * | 5/1996 | Edwards | A61N 1/403 606/41 |
| 5,599,346 A * | 2/1997 | Edwards | A61N 5/045 606/41 |
| 5,733,282 A | 3/1998 | Ellman et al. | |
| 5,792,135 A | 8/1998 | Madhani et al. | |
| 5,800,378 A * | 9/1998 | Edwards | A61N 1/40 606/45 |
| 5,823,197 A * | 10/1998 | Edwards | A61B 18/148 606/41 |
| 5,843,021 A * | 12/1998 | Edwards | A61B 18/18 604/22 |
| 5,913,855 A * | 6/1999 | Gough | A61B 18/1477 606/49 |
| 6,045,549 A | 4/2000 | Smethers, II | |
| 6,109,268 A | 8/2000 | Thapliyal et al. | |
| 6,139,545 A | 10/2000 | Utley et al. | |
| 6,210,355 B1 | 4/2001 | Edwards et al. | |
| 6,361,531 B1 | 3/2002 | Hissong | |
| 6,416,512 B1 | 7/2002 | Ellman et al. | |
| 6,447,510 B1 | 9/2002 | Ellman et al. | |
| 6,526,318 B1 | 3/2003 | Ansarinia | |
| 6,562,036 B1 | 5/2003 | Ellman et al. | |
| 6,572,613 B1 | 6/2003 | Ellman et al. | |
| 6,911,027 B1 | 6/2005 | Edwards et al. | |
| 6,920,883 B2 | 7/2005 | Bessette et al. | |
| 7,001,380 B2 | 2/2006 | Goble | |
| 7,004,941 B2 | 2/2006 | Tvinnereim et al. | |
| 7,297,143 B2 | 11/2007 | Woloszko et al. | |
| 7,377,918 B2 | 5/2008 | Amoah | |
| 7,491,200 B2 | 2/2009 | Underwood | |
| 7,720,521 B2 | 5/2010 | Chang et al. | |
| 7,842,034 B2 | 11/2010 | Mittelstein et al. | |
| 7,862,560 B2 | 1/2011 | Marion | |
| 7,892,230 B2 | 2/2011 | Woloszko | |
| 8,290,582 B2 | 10/2012 | Lin et al. | |
| 8,298,243 B2 | 10/2012 | Carlton et al. | |
| 8,479,969 B2 | 7/2013 | Shelton, IV | |
| 8,512,335 B2 | 8/2013 | Cheng et al. | |
| 8,573,465 B2 | 11/2013 | Shelton, IV | |
| 8,747,401 B2 | 6/2014 | Gonzalez et al. | |
| 8,783,541 B2 | 7/2014 | Shelton, IV et al. | |
| 8,800,838 B2 | 8/2014 | Shelton, IV | |
| 8,900,227 B2 | 12/2014 | Stierman | |
| 8,936,594 B2 | 1/2015 | Wolf et al. | |
| 8,961,510 B2 | 2/2015 | Alshemari | |
| 8,979,842 B2 | 3/2015 | McNall, III et al. | |
| 9,011,428 B2 | 4/2015 | Nguyen et al. | |
| 9,072,597 B2 | 7/2015 | Wolf et al. | |
| 9,393,067 B2 | 7/2016 | van der Burg et al. | |
| 9,415,194 B2 | 8/2016 | Wolf et al. | |
| 9,474,915 B2 | 10/2016 | Gonzales et al. | |
| 9,532,796 B2 | 1/2017 | DuBois et al. | |
| 9,649,144 B2 | 5/2017 | Aluru et al. | |
| 9,687,288 B2 * | 6/2017 | Saadat | G01M 3/24 |
| 10,028,781 B2 | 7/2018 | Saadat | |
| 2003/0208250 A1 | 11/2003 | Edwards et al. | |
| 2004/0204747 A1 | 10/2004 | Kemeny et al. | |
| 2005/0080410 A1 | 4/2005 | Rioux et al. | |
| 2005/0283148 A1 | 12/2005 | Janssen et al. | |
| 2006/0004323 A1 | 1/2006 | Chang et al. | |
| 2006/0052776 A1 | 3/2006 | Desinger et al. | |
| 2006/0178670 A1 | 8/2006 | Woloszko et al. | |
| 2007/0027451 A1 | 2/2007 | Desinger et al. | |
| 2007/0073282 A1 | 3/2007 | McGaffigan et al. | |
| 2008/0027423 A1 | 1/2008 | Choi et al. | |
| 2008/0027505 A1 | 1/2008 | Levin et al. | |
| 2010/0274164 A1 | 10/2010 | Juto | |
| 2011/0160740 A1 | 6/2011 | Makower et al. | |
| 2012/0029498 A1 | 2/2012 | Branovan | |
| 2012/0101494 A1 | 4/2012 | Cadouri et al. | |
| 2012/0316557 A1 | 12/2012 | Sartor et al. | |
| 2014/0100557 A1 | 4/2014 | Bohner et al. | |
| 2014/0324037 A1 | 10/2014 | Hoey et al. | |
| 2014/0364725 A1 | 12/2014 | Makower | |
| 2016/0058495 A1 | 3/2016 | Twomey | |
| 2016/0058500 A1 | 3/2016 | Sharp et al. | |
| 2016/0256181 A1 | 9/2016 | Allen, IV et al. | |
| 2016/0331459 A1 | 11/2016 | Townley et al. | |
| 2017/0165459 A1 | 6/2017 | Gross et al. | |
| 2017/0197075 A1 | 7/2017 | Van Bruggen et al. | |
| 2017/0231474 A1 | 8/2017 | Saadat et al. | |
| 2018/0078327 A1 | 3/2018 | Lin et al. | |
| 2018/0103994 A1 | 4/2018 | Fox et al. | |
| 2018/0116711 A1 | 5/2018 | Suh | |
| 2018/0133460 A1 | 5/2018 | Townley et al. | |
| 2018/0177541 A1 | 6/2018 | Regadas | |
| 2018/0177546 A1 | 6/2018 | Dinger et al. | |
| 2018/0193052 A1 | 7/2018 | Govari et al. | |
| 2018/0228533 A1 | 8/2018 | Wolf et al. | |
| 2018/0263678 A1 | 9/2018 | Saadat | |
| 2019/0083157 A1 | 3/2019 | Saadat | |
| 2019/0374280 A1 | 12/2019 | Salazar et al. | |

FOREIGN PATENT DOCUMENTS

| | | |
|---|---|---|
| EP | 1049413 A1 | 11/2000 |
| EP | 1189543 A1 | 3/2002 |
| EP | 1416870 A4 | 5/2004 |
| EP | 3027133 A4 | 6/2016 |
| EP | 3030183 A1 | 6/2016 |
| EP | 3157454 B1 | 4/2017 |
| EP | 3258864 A1 | 12/2017 |
| WO | WO 1999/003411 A1 | 1/1999 |
| WO | WO 1999/030655 A1 | 6/1999 |
| WO | WO 2001/012089 A1 | 2/2001 |
| WO | WO 2008/079476 A2 | 7/2008 |
| WO | WO 2011/005903 A2 | 1/2011 |
| WO | WO 2011/025830 A1 | 3/2011 |
| WO | WO 2018/075273 A1 | 4/2018 |

OTHER PUBLICATIONS

Gindros, George, et al. "Mucosal changes in chronic hypertrophic rhinitis after surgical turbinate reduction." *European archives of oto-rhino-laryngology* 266.9 (2009): 1409-1416.
Ho, Ki-Hong Kevin, et al. "Electromechanical reshaping of septal cartilage." *The Laryngoscope* 113.11 (2003): 1916-1921.
International Search Report and Written Opinion dated Jul. 2, 2020 for International Application No. PCT/IB2020/052811, 16 pages.

(56) References Cited

OTHER PUBLICATIONS

U.S. Appl. No. 62/806,009, entitled "Instrument for Endoscopic Posterior Nasal Nerve Ablation," filed Feb. 15, 2019.

* cited by examiner

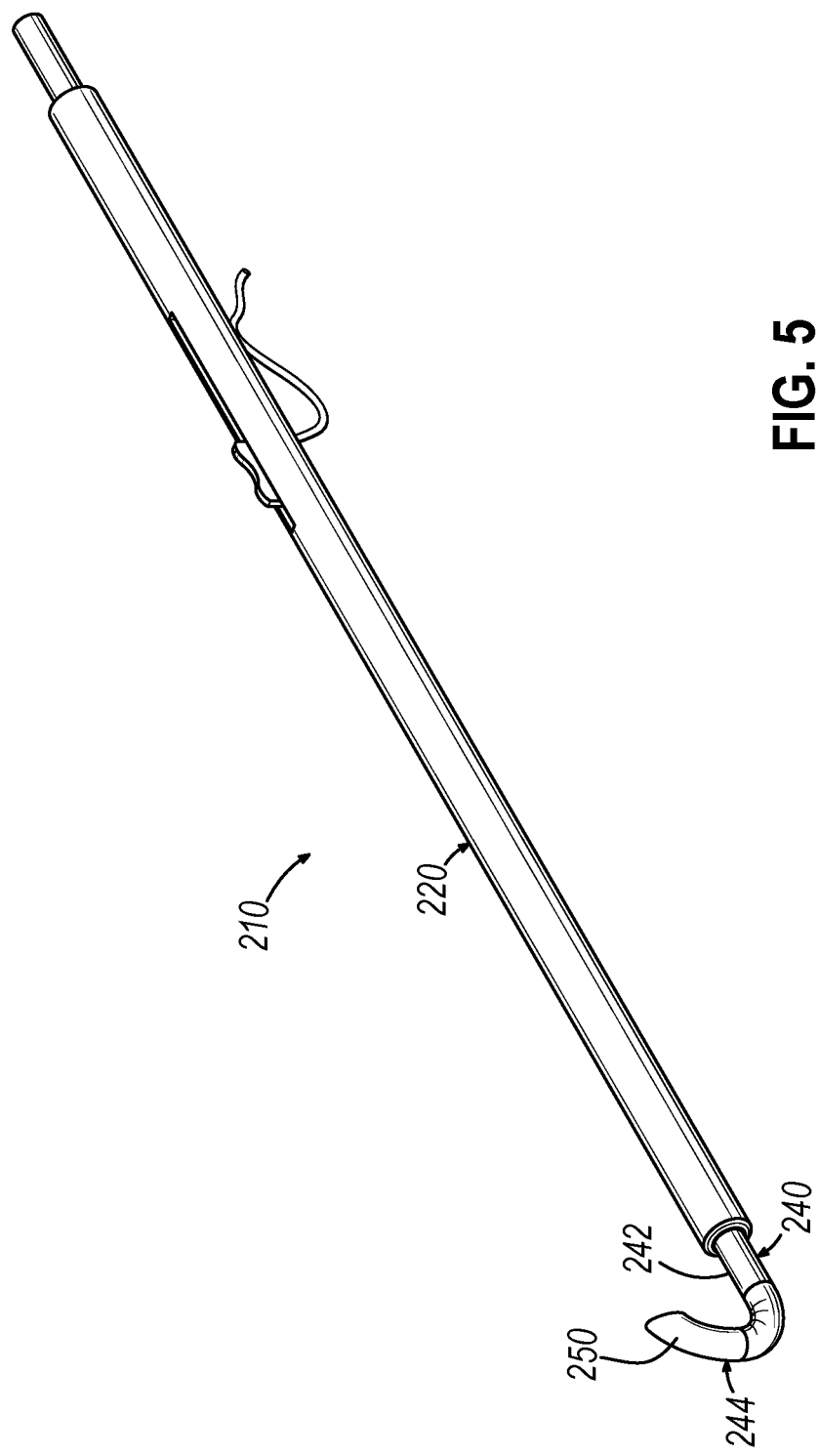

NEEDLE INSTRUMENT FOR POSTERIOR NASAL NEURECTOMY ABLATION

PRIORITY

This application claims priority to U.S. Provisional Patent App. No. 62/829,068, entitled "Needle Instrument for Posterior Nasal Neurectomy Ablation," filed Apr. 4, 2019, the disclosure of which is incorporated by reference herein.

BACKGROUND

Rhinitis is a medical condition that presents as irritation and inflammation of the mucous membrane within the nasal cavity. The inflammation results in the generation of excessive amounts of mucus, which can cause runny nose, nasal congestion, sneezing, and/or post-nasal drip. Allergenic rhinitis is an allergic reaction to environmental factors such as airborne allergens, while non-allergenic (or "vasomotor") rhinitis is a chronic condition that presents independently of environmental factors. Conventional treatments for rhinitis include antihistamines, topical or systemic corticosteroids, and topical anticholinergics, for example.

For cases of intractable rhinitis in which the symptoms are severe and persistent, an additional treatment option is the surgical removal of a portion of the vidian (or "pterygoid") nerve—a procedure known as vidian neurectomy. The theoretical basis for vidian neurectomy is that rhinitis is caused by an imbalance between parasympathetic and sympathetic innervation of the nasal cavity, and the resultant over stimulation of mucous glands of the mucous membrane. Vidian neurectomy aims to disrupt this imbalance and reduce nasal mucus secretions via surgical treatment of the vidian nerve. However, in some instances, vidian neurectomy can cause collateral damage to the lacrimal gland, which is innervated by the vidian nerve. Such damage to the lacrimal gland has been known to result in long-term health complications for the patient, such as chronic dry eye. Posterior nasal neurectomy, or surgical removal of a portion of the posterior nasal nerves, is known as an effective alternative to vidian neurectomy for treating intractable rhinitis.

FIG. 1 depicts a left sagittal view of a portion of a patient's head, showing the nasal cavity (10), the frontal sinus (12), the sphenoid sinus (14), and the sphenoid bone (16). The nasal cavity (10) is bounded laterally by the nasal wall (18), which includes an inferior turbinate (20), a middle turbinate (22), and a superior turbinate (24). The vidian nerve (32) resides within the vidian (or "pterygoid") canal (30), which is defined in part by the sphenoid bone (16) and is located posterior to the sphenoid sinus (14), approximately in alignment with the middle turbinate (22). The vidian nerve (32) is formed at its posterior end by the junction of the greater petrosal nerve (34) and the deep petrosal nerve (36), and joins at its anterior end with the pterygopalatine ganglion (38), which is responsible for regulating blood flow to the nasal mucosa. The posterior nasal nerves (40) join with the pterygopalatine ganglion (38) and extend through the region surrounding the inferior turbinate (20).

While instruments and method for performing vidian neurectomies and posterior nasal neurectomies are known, it is believed that no one prior to the inventors has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

FIG. 5 depicts a perspective view of another exemplary RF ablation instrument suitable for use with the RF surgical system of FIG. 2;

Figure 1:
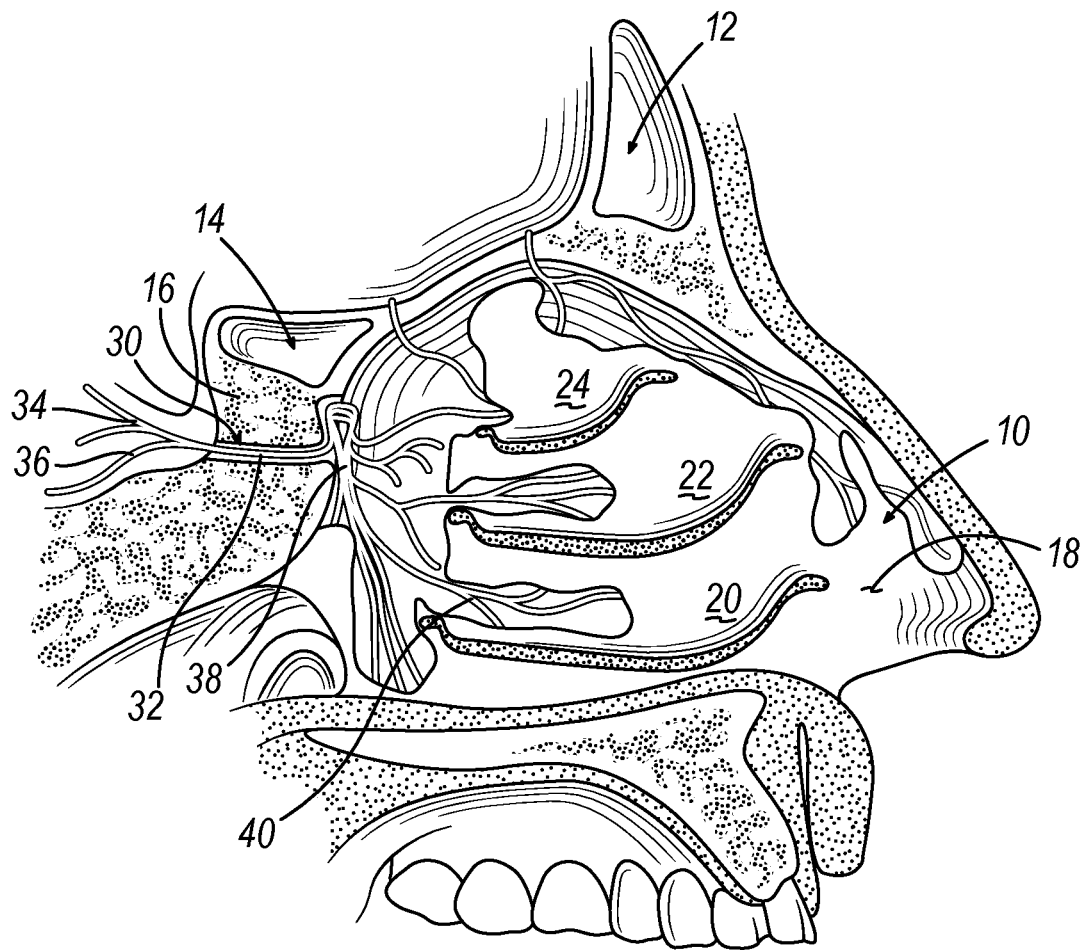
FIG. 1 depicts a left sagittal view of a portion of a patient's head, showing details of certain paranasal sinuses and nerves, including the vidian nerve and the posterior nasal nerve.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical instrument having a distal surgical end effector. The term "proximal" refers to the position of an element arranged closer to the surgeon, and the term "distal" refers to the position of an element arranged closer to the surgical end effector of the surgical instrument and further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

As used herein, the terms "about," "approximately," and the like in connection with any numerical values or ranges of values are intended to encompass the exact value(s) referenced, as well as a suitable dimensional tolerance that enables the referenced feature or combination of features to function for the intended purpose described herein.

I. EXEMPLARY RF ABLATION SURGICAL SYSTEM HAVING INSTRUMENT WITH EXTENDABLE ABLATION NEEDLE

In some instances, it may be desirable to provide an RF ablation instrument having an ablation needle that is selectively actuatable between retracted and extended positions to facilitate effective and safe RF ablation of a nasal nerve, such as the posterior nasal nerve (40) as an alternative to a traditional vidian neurectomy procedure. Each of the exemplary RF ablation instruments (110, 210, 310) described below functions in such a manner.

Figure 2:
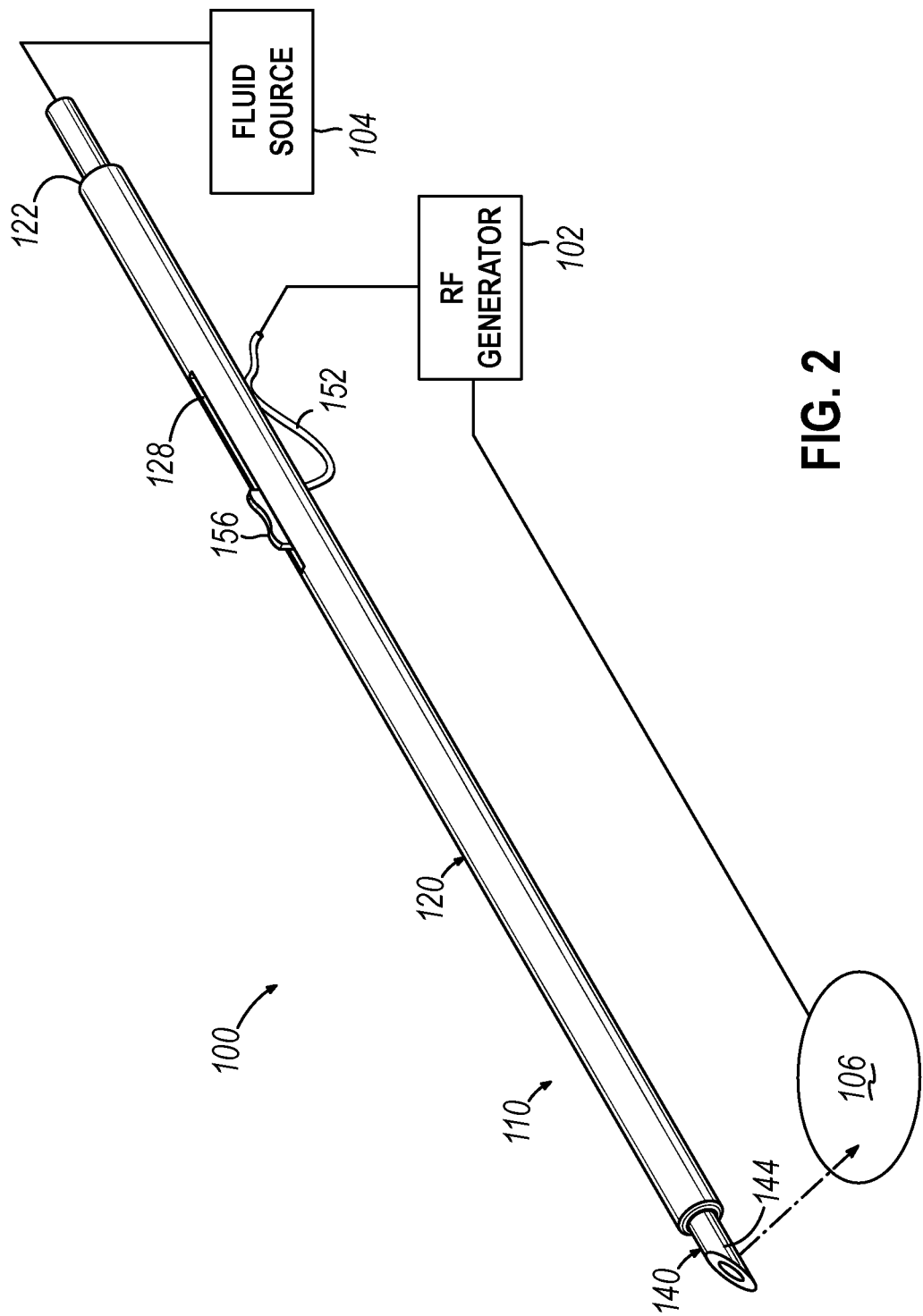
FIG. 2 depicts a schematic perspective view of an exemplary surgical system that includes an RF ablation instrument.

FIG. 2 shows an exemplary RF ablation surgical system (100) operable to ablate a nerve, such as the posterior nasal nerve (40), within the nasal cavity (10) of a patient with radio frequency (RF) energy. Surgical system (100) comprises an RF ablation instrument (110) having an outer tube (120) and an inner ablation needle (140) slidably disposed coaxially within outer tube (120), an RF generator (102) electrically coupled with the ablation needle (140), and a fluid source (104) fluidly coupled with a central lumen of ablation needle (140). System (100) of the present example further comprises an RF ground pad (106) electrically coupled with RF generator (102) to enable monopolar RF ablation of tissue (e.g., a nerve) positioned in electrical contact with an electrode disposed at a distal tip (144) of ablation needle (140), as described in greater detail below. Fluid source (104) is configured to deliver a fluid to the central lumen of ablation needle (140), which dispenses the fluid to tissue being ablated to regulate a temperature of the tissue and optionally also enhance electrical coupling of the electrode with the tissue.

Figure 3:
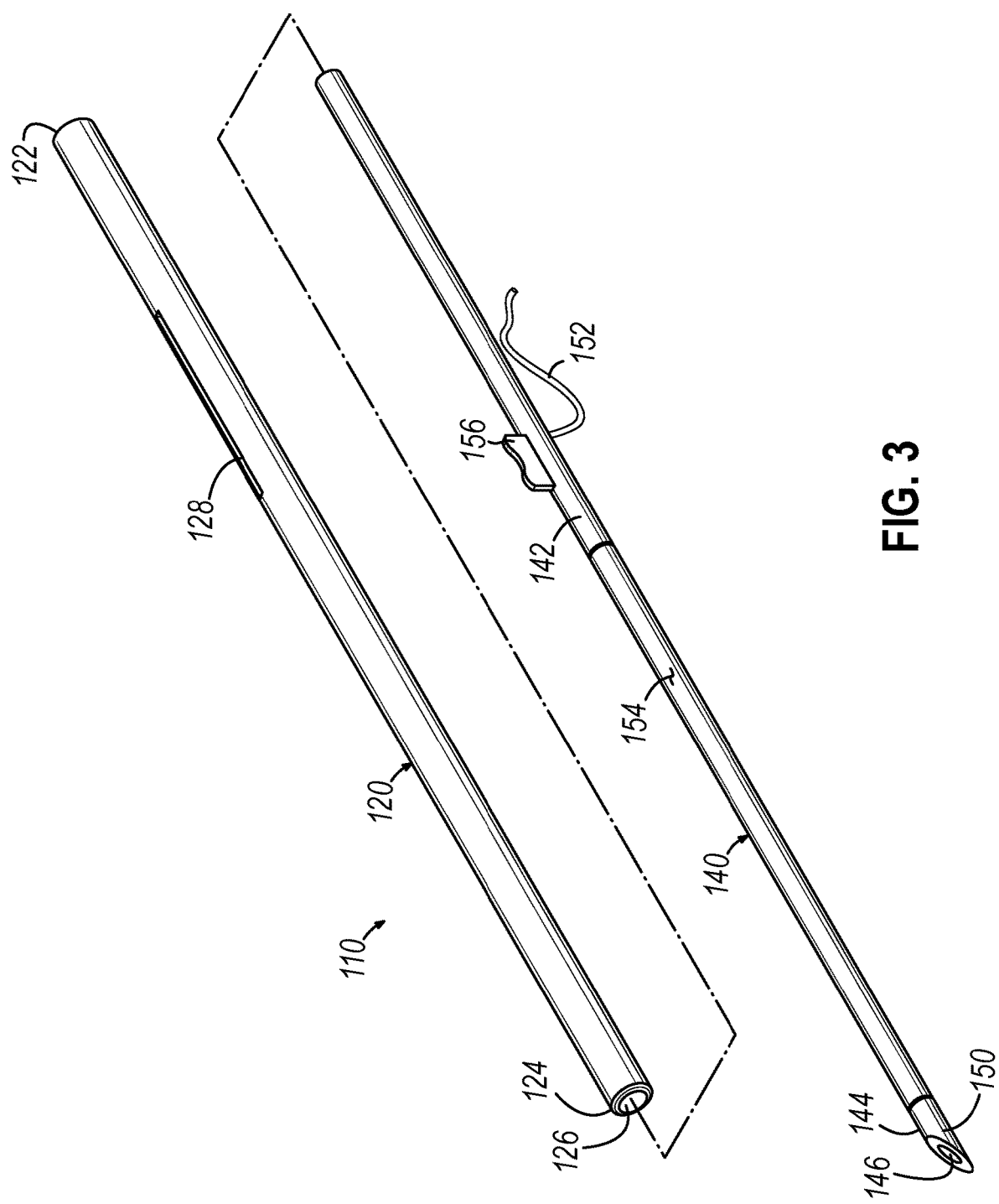
FIG. 3 depicts a disassembled perspective view of the RF ablation instrument of FIG. 2, showing an outer tube and an inner needle of the RF ablation instrument.
Figure 4A:
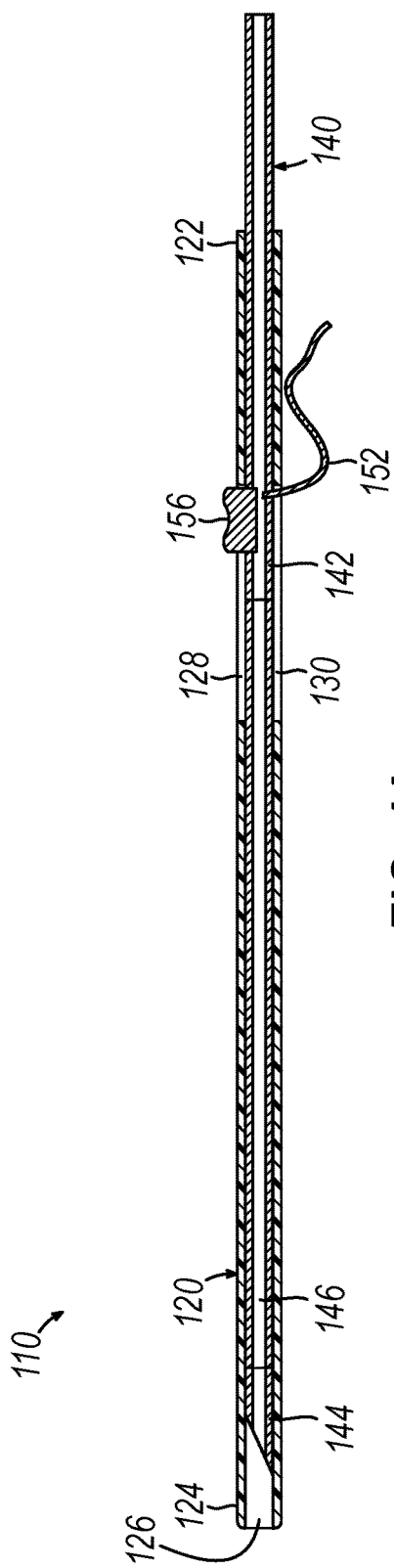
FIG. 4A depicts a side cross-sectional view of the RF ablation instrument of FIG. 2, showing the inner needle in a proximal retracted position relative to the outer tube.
Figure 4B:
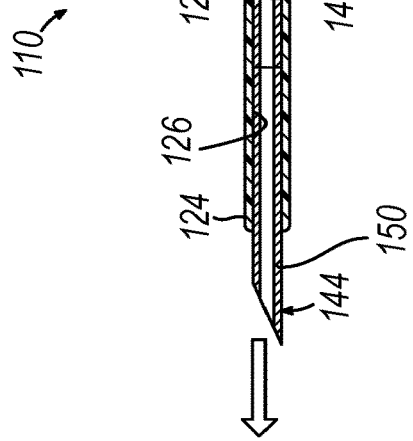
FIG. 4B depicts a side cross-sectional view of the RF ablation instrument of FIG. 2, showing the inner needle in a distal extended position relative to the outer tube.

As shown in FIGS. 3-4B, outer tube (120) of RF ablation instrument (110) includes a proximal end (122), a distal end (124), and a tube lumen (126) extending therebetween. Tube lumen (126) is sized to slidably receive ablation needle (140) therein, as described below. A proximal portion of outer tube (120) includes a first longitudinal slot (128) extending laterally through a first side of outer tube (120), and a second longitudinal slot (130) (see FIGS. 4A-4B) extending laterally through an opposed second side of outer tube (120).

Ablation needle (140) includes an elongate shaft (142) defining a proximal end of needle (140), and a distal tip (144) extending distally from needle shaft (142) and defining a distal end of ablation needle (140). Distal tip (144) terminates distally at a sharped point configured to pierce tissue. A needle lumen (146) extends longitudinally through an entirety of needle (140), such that needle lumen (146) opens distally at distal tip (144). As described below, needle lumen (146) is configured to fluidly couple with fluid source (104) to communicate fluid from fluid source (104) to tissue being ablated by ablation needle (140). Needle distal tip (144) of the present example extends coaxially with needle shaft (142) and outer tube (120). In other versions, needle distal tip (144) may be pre-formed with a shape that extends non-coaxially relative to needle shaft (142). In such versions, needle distal tip (144) may be resiliently biased toward such a pre-formed shape yet remain deflectable toward a straight configuration in coaxial alignment with needle shaft (142) and outer tube (210), for example as described below in connection with FIGS. 5-8B.

Ablation needle (140) further comprises an electrode (150) disposed at needle distal tip (144). Electrode (150) is configured to deliver RF energy from RF generator (102) to tissue positioned in electrical contact with electrode (150), to thereby ablate the tissue with RF energy. In the present version, needle distal tip (144) and needle shaft (142) are formed of an electrically conductive material, such as nickel-titanium alloy (or "Nitinol") or spring steel, such that needle distal tip (144) itself defines electrode (150) and needle shaft (142) functions as a conductor that delivers RF energy to needle distal tip (144). An electrical connector (152) is affixed to a proximal portion of needle shaft (142) and is configured to electrically couple with RF generator to deliver RF energy to electrode (150) via needle shaft (142). In other versions, needle distal tip (144) and/or needle shaft (142) may be formed of a non-conductive material, and/or electrode (150) may formed separately from and affixed to needle distal tip (144). In some such versions, electrode (150) may be electrically coupled with electrical connector (152) via a conductor not defined by needle shaft (142), such as a wire (not shown).

As described above, RF ablation instrument (110) of the present example includes a single electrode (150) defined at needle distal tip (144). As shown in FIG. 2, electrode (150) is configured to cooperate with RF ground pad (106) to treat tissue with monopolar RF energy. Such a configuration advantageously provides sufficient energy levels needed for effective RF ablation of the posterior nasal nerve (40). However, it will be appreciated that in other versions, RF ground pad (106) may be omitted from surgical system (100) and needle distal tip (144) may be provided with a pair of electrodes (150) configured to cooperate to treat various types of tissue (e.g., other than the posterior nasal nerve (40)) with bipolar RF energy. Such a configuration may be configured and operable in accordance with any one or more of the teachings of U.S. Pat. App. No. 62/806,009, entitled "Instrument for Endoscopic Posterior Nasal Nerve Ablation," filed Feb. 15, 2019, the disclosure of which is incorporated by reference herein.

Additionally, in some versions, needle distal tip (144) may further include one or more tissue sensors operable to sense a condition of the tissue (e.g., a nerve) being ablated by electrode (150). Each such sensor may communicate a signal to a processor (not shown) of surgical system (100) indicating the sensed condition. In response to receiving the signal, the system processor may then regulate (e.g., deactivate) the RF ablation energy being delivered to electrode (150) from RF generator (102), and/or provide an indication to the operator informing of the sensed tissue condition. In some versions, such a sensor may comprise a thermocouple operable to measure a temperature of the target tissue during ablation. In other versions, such a sensor may comprise a pair of detection electrodes operable to deliver a low power RF signal to the target tissue to measure an electrical impedance of the tissue during ablation. In some such versions, such detection electrodes may be provided separately from electrode (150). In other such versions, electrode (150) may be operable as both an ablation electrode and as a detection electrode. In either configuration, the low power RF signal may be delivered to the target tissue simultaneously or in rapidly alternating fashion with the high-power RF ablation energy delivered by electrode (150). While the target tissue remains substantially intact and unablated, the low power RF signal will pass freely through the tissue with a relatively low impedance. As ablation of the tissue progresses, the detection electrodes will detect an increase in impedance of the tissue, which is communicated to the system processor.

As shown best in FIG. 3, ablation needle (140) further comprises an electrically insulative layer (154) provided on an outer surface of needle shaft (142) and which extends longitudinally between electrical connector (152) and needle distal tip (144). Electrically insulative layer (154) is configured to prevent electrical shorting between needle shaft (142) and an inner surface of outer tube (120), particularly in versions in which both outer tube (120) and ablation needle (140) are formed of an electrically conductive material. A distal end of electrically insulative layer (154) terminates at a proximal end of needle distal tip (144), such that needle distal tip (144) is exposed for contact with tissue and thereby operable as electrode (150). In some versions, electrically insulative layer (154) may be applied to needle shaft (142) as a coating. In other versions, electrically insulative layer (154) may be formed on the inner surface of outer tube (120) defining tube lumen (126).

Ablation needle (140) further comprises a projection in the form of an elongate tab (156) projecting laterally outwardly from a proximal portion of needle shaft (142) generally in alignment with and opposed from electrical connector (152). Tab (156) is operable as an advancer to selectively actuate needle (140) longitudinally relative to outer tube (120). In that regard, ablation needle (140) is slidably housed within outer tube (120) such that advancer tab (156) projects laterally through first longitudinal slot (128), and such that electrical connector (152) projects laterally through second longitudinal slot (130). Advancer tab (156) and electrical connector (152) are fixed to needle shaft (142) such that advancer tab (156) slides longitudinally within first longitudinal slot (128) and electrical connector (152) simultaneously slides longitudinally within second longitudinal slot (130) as needle shaft (142) translates through tube lumen (126). Advancer tab (156) may be formed of a non-conductive material or otherwise be electrically insulated from electrical connector (152) and electrode (150).

As shown in FIGS. 4A and 4B, ablation needle (140) is actuatable via advancer tab (156) between a proximal retracted position (FIG. 4A) and a distal extended position (FIG. 4B) relative to outer tube (120). In the exemplary proximal retracted position of FIG. 4A, advancer tab (156) and electrical connector (152) are disposed at the proximal ends of longitudinal slots (128, 130), and needle distal tip (144) is concealed within the distal end of outer tube (120). In the exemplary distal extended position of FIG. 4B, advancer tab (156) and electrical connector (152) are disposed at the distal ends of longitudinal slots (128, 130), and needle distal tip (144) is exposed from outer tube (120) so as to extend distally beyond the distal end of outer tube (120). As shown, ablation needle (140) of the present example is formed with a sufficient length such that the proximal end of needle (140) extends proximally of proximal end (122) of outer tube (120) in both of the extended and retracted positions, thus enabling needle (140) to remain coupled with fluid source (104). As described in greater detail below in connection with FIGS. 9A-9C, ablation needle (140) is configured to be actuated from the proximal retracted position to the distal extended position to pierce the nasal wall (18) of a patient following insertion of the distal end of RF ablation instrument (110) into the nasal cavity (10).

II. EXEMPLARY ALTERNATIVE RF ABLATION INSTRUMENTS HAVING SHAPED RESILIENT NEEDLE TIPS

In some instances, it may be desirable to configure ablation needle (140) of RF ablation instrument (110) such that needle distal tip (144) is resiliently biased toward a pre-formed shape that is offset from the longitudinal axis of needle shaft (142), such that needle distal tip (144) is non-coaxial with needle shaft (142) and outer tube (120) when distal needle tip (144) is extended distally from outer tube (120). In such an offset configuration, needle distal tip (144) is oriented away from the longitudinal axis of shaft (142) and is thus better suited to easily access a particular portion of a body cavity in which needle distal tip (144) is positioned, such as the nasal cavity (10), without having to flex or bend needle shaft (142).

FIG. 5 shows an exemplary alternative RF ablation instrument (210) suitable for use with surgical system (100) in place of RF ablation instrument (110). RF ablation instrument (210) is similar to RF ablation instrument (110) described above except as otherwise described below. Like RF ablation instrument (110), RF ablation instrument (210) includes an outer tube (220) and an ablation needle (240) slidably disposed within outer tube (220). Ablation needle (240) includes an elongate needle shaft (242) arranged coaxially with outer tube (220), and a needle distal tip (244) having an electrode (250) configured to ablate tissue with monopolar RF energy. Unlike needle distal tip (144), needle distal tip (244) is resiliently biased toward a pre-formed curved shape such that needle distal tip (244) is oriented away from the longitudinal axis of needle shaft (242), in a non-coaxial relationship with needle shaft (242) and outer tube (220).

Figure 6A:
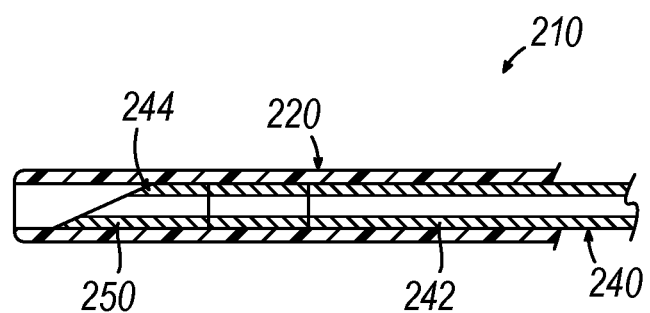
FIG. 6A depicts a side cross-sectional view of a distal portion of the RF ablation instrument of FIG. 5, showing an inner needle in a proximal retracted position relative to an outer tube.
Figure 6B:
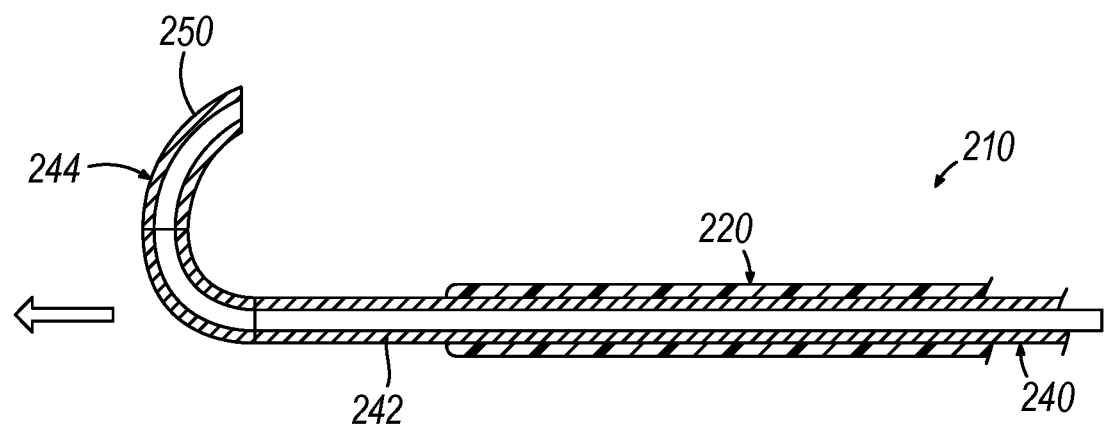
FIG. 6B depicts a side cross-sectional view of a distal portion of the RF ablation instrument of FIG. 5, showing the inner needle in a distal extended position relative to the outer tube.

As shown in FIG. 6A, needle distal tip (244) is configured to resiliently deform to a straight configuration coaxial with needle shaft (242) and outer tube (220) when ablation needle (240) is in the proximal retracted position relative to outer tube (220). As shown in FIG. 6B, distal needle tip (244) is configured to resiliently transition from the straight configuration to its natural curved configuration in which distal needle tip (244) is non-coaxial with needle shaft (242) and outer tube (220), in response to distal extension of needle (240) that exposes distal needle tip (244) from outer tube (220). Advantageously, such an arrangement enables distal needle tip (244) to be safely housed within outer tube (220) during insertion of the distal end of RF ablation instrument (210) into a patient's body cavity, while also enabling distal needle tip (244) to assume an orientation that promotes effective access to a target ablation site thereafter.

Figure 7:
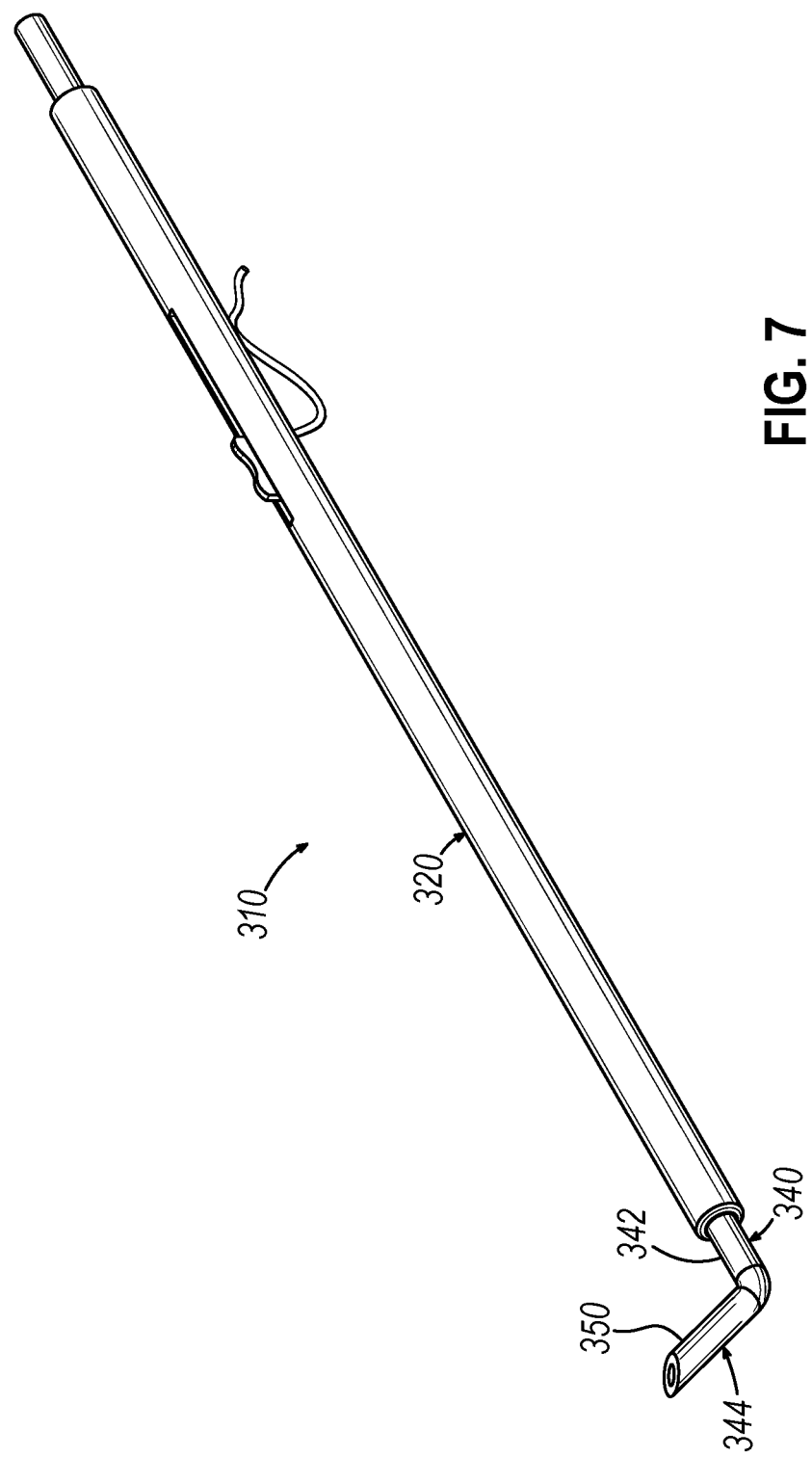
FIG. 7 depicts a perspective view of another exemplary RF ablation instrument suitable for use with the RF surgical system of FIG. 2.

FIG. 7 shows another exemplary alternative RF ablation instrument (310) suitable for use with surgical system (100) in place of RF ablation instrument (110). RF ablation instrument (310) is similar to RF ablation instruments (110, 210) described above except as otherwise described below. Like RF ablation instruments (110, 210), RF ablation instrument (310) includes an outer tube (320) and an ablation needle (340) slidably disposed within outer tube (320). Ablation needle (340) includes an elongate needle shaft (342) arranged coaxially with outer tube (320), and a distal needle tip (344) having an electrode (350) configured to ablate tissue with monopolar RF energy. Similar to needle distal tip (244), needle distal tip (344) is resiliently biased toward a pre-formed configuration in which needle distal tip (344) is oriented away from the longitudinal axis of needle shaft (342). In particular, needle distal tip (344) is resiliently biased toward an angled configuration in which needle distal tip (344) extends angularly relative to needle shaft (342) in a non-coaxial relationship with needle shaft (342) and outer tube (320).

Figure 8A:
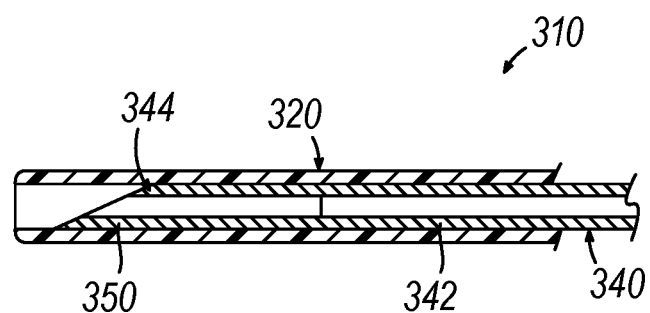
FIG. 8A depicts a side cross-sectional view of a distal portion of the RF ablation instrument of FIG. 7, showing an inner needle in a proximal retracted position relative to an outer tube.
Figure 8B:
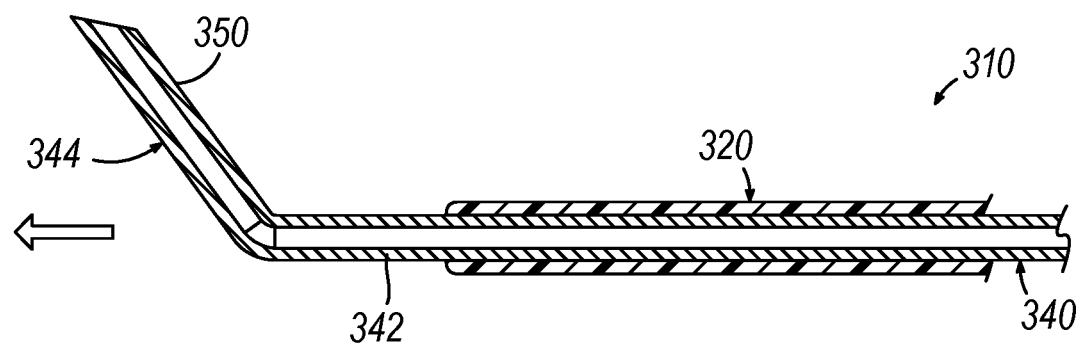
FIG. 8B depicts a side cross-sectional view of a distal portion of the RF ablation instrument of FIG. 7, showing the inner needle in a distal extended position relative to the outer tube.

As shown in FIG. 8A, needle distal tip (344) is configured to resiliently deform to a straight configuration coaxial with needle shaft (342) and outer tube (320) when ablation needle (340) is in the proximal retracted position relative to outer tube (320). As shown in FIG. 6B, needle distal tip (344) is configured to resiliently transition from the straight configuration to its natural curved configuration in response to distal extension of needle (340) that exposes needle distal tip (344) from outer tube (320).

III. EXEMPLARY METHOD OF ABLATING POSTERIOR NASAL NERVE

Having described exemplary features of RF ablation surgical system (100) and RF ablation instruments (110, 210, 310) above, an exemplary method of performing a neurectomy on a posterior nasal nerve (40) of a patient with system (100) will now be described in connection with FIGS. 9A-9C. While the exemplary method is showing being performed with RF ablation instrument (110), it will be appreciated that similar methods may be performed using RF ablation instruments (110, 210, 310). Additionally, while surgical system (100) is shown and described for treating a posterior nasal nerve, it will be appreciated that surgical system (100) may be employed in various other surgical applications for ablating other nerves within the nasal cavity (10), or for ablating tissues in various other anatomical regions of a patient. For instance, the teachings herein may be combined with at least some of the teachings of U.S. Pat. Pub. No. 2019/0374280, entitled "Apparatus and Method for Performing Vidian Neurectomy Procedure," published Dec. 12, 2019, the disclosure of which is incorporated by reference herein.

Figure 9A:
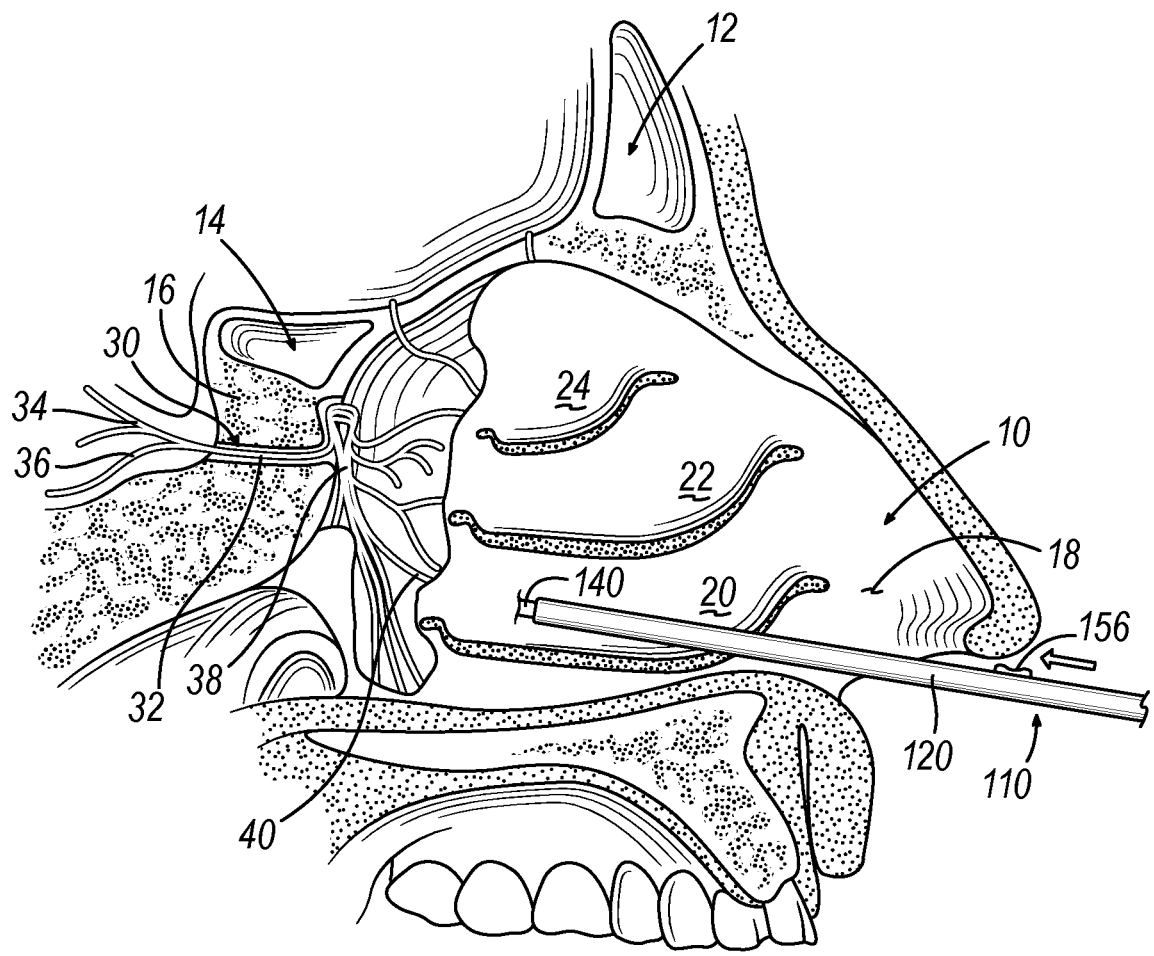
FIG. 9A depicts a left sagittal view of a portion of a patient's head, showing insertion of an RF surgical instrument into the patient's nasal cavity and distal extension of the inner needle relative to the outer tube to pierce the nasal wall in the region of a posterior nasal nerve.
Figure 9B:
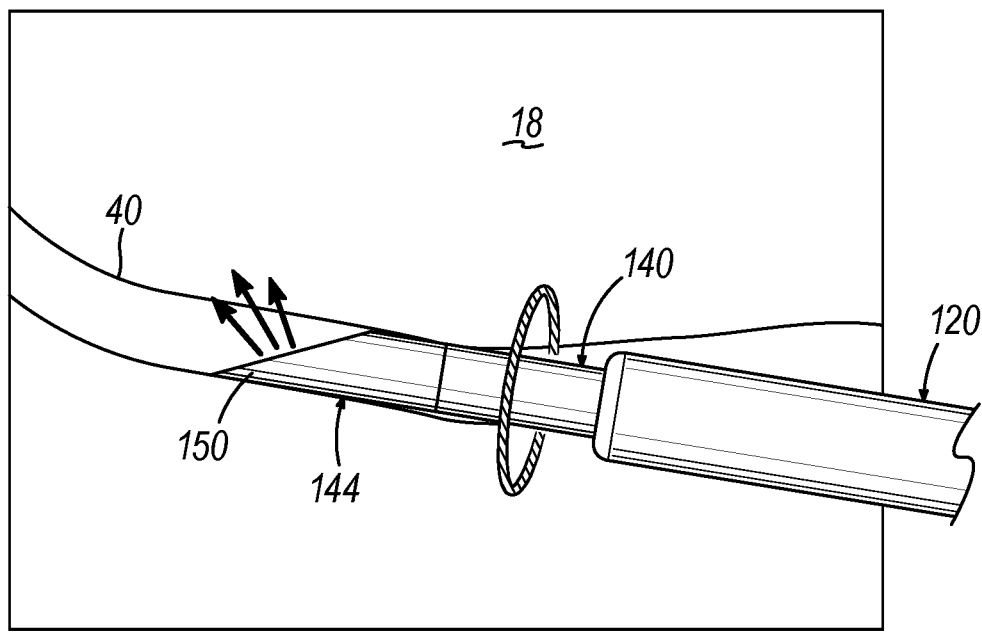
FIG. 9B depicts an enlarged schematic side view of a distal portion of the RF ablation instrument of FIG. 9A in the distal extended position, showing a distal end of the needle delivering RF energy and liquid to a portion of the posterior nasal nerve beneath the nasal wall surface to thereby ablate the nerve portion.
Figure 9C:
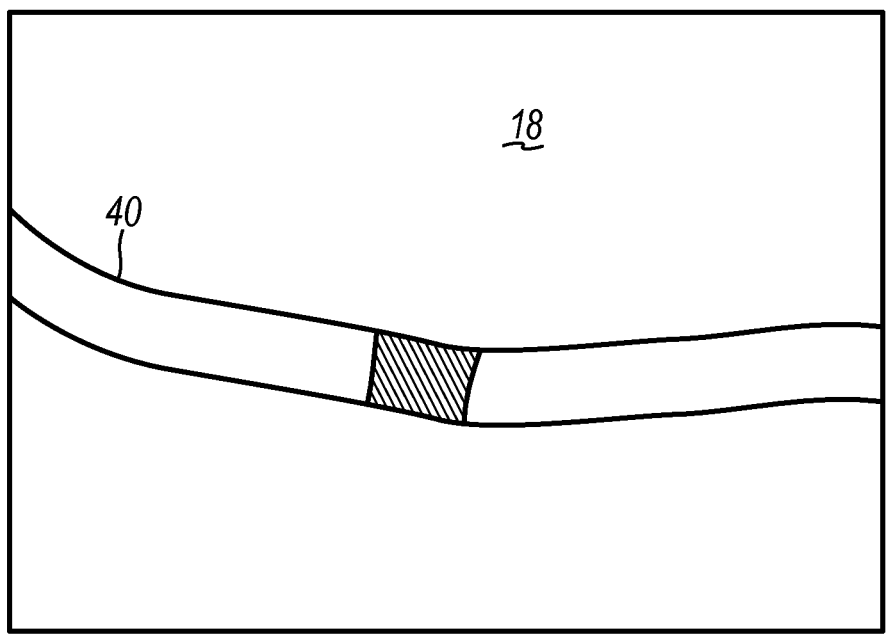
FIG. 9C depicts a schematic side view of the posterior nasal nerve of FIG. 9B, showing the targeted portion of the nerve following RF ablation by the RF surgical instrument.

As shown in FIG. 9A, the distal end of RF ablation instrument is inserted into the nasal cavity (10) and is toward the posterior ends of the inferior and middle turbinates (20, 22), which may be performed under visualization provided by an endoscope (not shown), for example. Upon reaching a target site of the nasal wall (18) in which a target portion of the posterior nasal nerve (40) resides, the operator advances advancer tab (156) distally to thereby extend ablation needle (140) and pierce nasal wall (18) with needle distal tip (144). As shown in FIGS. 9B and 9C, electrode (150) is then energized with monopolar RF energy to thereby ablate a portion posterior nasal nerve (40). Simultaneously, needle distal tip (144) delivers fluid from needle lumen (146) to the ablation site to thereby regulate a temperature of posterior nasal nerve (40) and surrounding nasal tissue during ablation. As described above, the dispensed fluid may also function to enhance electrical coupling between electrode (150) and posterior nasal nerve (40).

Though not shown herein, any one or more of RF ablation instruments (110, 210, 310) described above may be combined with features of an image-guided surgery (IGS) navigation system to further facilitate positioning of needle distal tip (144) within a patient. By way of example, such an IGS navigation system may be constructed and operable in accordance with at least some of the teachings of U.S. Pat. No. 7,720,521, entitled "Methods and Devices for Performing Procedures within the Ear, Nose, Throat and Paranasal Sinuses," issued May 18, 2010, the disclosure of which is incorporated by reference herein; and/or U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein.

IV. EXEMPLARY COMBINATIONS

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument comprising: (a) an outer tube configured to be gripped by a user; and (b) a needle slidably disposed within the outer tube, wherein the needle comprises: (i) a needle lumen, (ii) a distal needle tip configured to pierce tissue, wherein the needle lumen opens to the distal needle tip such that the distal needle tip is configured to deliver fluid from the needle lumen to tissue, and (iii) an electrode disposed at the distal needle tip, wherein the electrode is operable to deliver RF energy to tissue for ablating the tissue, wherein the needle is translatable relative to the outer tube between a proximal retracted position in which the distal needle tip is housed coaxially within the outer tube, and a distal extended position in which the distal needle tip is exposed from the outer tube and configured to pierce tissue.

Example 2

The surgical instrument of Example 1, wherein the electrode is configured to deliver monopolar RF energy to tissue when the needle is in the distal extended position.

Example 3

The surgical instrument of any of the preceding Examples, wherein the distal needle tip comprises an electrically conductive material that defines the electrode.

Example 4

The surgical instrument of any of the preceding Examples, further comprising an electrically insulative layer positioned between an outer surface of the needle and an inner surface of the outer tube.

Example 5

The surgical instrument of Example 4, wherein the electrically insulative layer is secured to the needle such that a distal end of the electrically insulative layer terminates proximally of the distal needle tip.

Example 6

The surgical instrument of any of the preceding Examples, wherein a proximal end of the needle is configured to couple with a fluid source, wherein the needle lumen is configured to communicate fluid from the fluid source to tissue through the distal needle tip.

Example 7

The surgical instrument of any of the preceding Examples, wherein the needle further comprises a needle shaft that extends longitudinally along a shaft axis, wherein the distal needle tip extends distally from the needle shaft and is resiliently biased toward an offset configuration in which the distal needle tip is non-coaxial with the shaft axis.

Example 8

The surgical instrument of Example 7, wherein an opening of the distal needle tip is oriented away from the shaft axis in the offset configuration.

Example 9

The surgical instrument of any of Examples 7 through 8, wherein the offset configuration comprises at least one of a curved configuration or an angled configuration.

Example 10

The surgical instrument of any of the preceding Examples, wherein the needle further comprises an electrical connector, wherein the electrical connector is configured to electrically couple with an RF energy source.

Example 11

The surgical instrument of any of the preceding Examples, wherein the needle further comprises a lateral projection, wherein the outer tube includes a longitudinal slot that slidably receives the lateral projection, wherein the lateral projection is exposed through the longitudinal slot such that the lateral projection is configured to be engaged by a user to actuate the needle relative to the outer tube.

Example 12

The surgical instrument of any of the preceding Examples, wherein the needle further comprises: (i) a first projection extending laterally from a first portion of the needle, and (ii) a second projection extending laterally from a second portion of the needle, wherein the outer tube comprises: (i) a first longitudinal slot configured to slidably receive the first projection therethrough, and (ii) a second longitudinal slot configured to slidably receive the second projection therethrough.

Example 13

The surgical instrument of Example 12, wherein the first projection comprises an actuator tab, wherein the second projection comprises an electrical connector.

Example 14

The surgical instrument of any of the preceding Examples, wherein the outer tube and the needle are configured to extend coaxially along a central axis of the surgical instrument when the needle is in the proximal retracted position.

Example 15

A surgical system comprising: (a) the surgical instrument of any of the preceding claims; (b) an RF energy source operatively coupled with the electrode of the needle; (c) a fluid source operatively coupled with the needle lumen; and (d) a ground pad operatively coupled with the RF energy source, wherein the surgical instrument is operable to energize the electrode with RF energy from the RF energy source while dispensing fluid from the fluid source through the distal needle tip, wherein the electrode is configured to cooperate with the ground pad to deliver monopolar RF energy to tissue for ablating the tissue.

Example 16

A surgical instrument comprising: (a) an outer tube; and (b) a needle slidably disposed within the outer tube, wherein the needle comprises: (i) a shaft defining a longitudinal shaft axis, (ii) a distal tip configured to pierce tissue, wherein the distal tip is resiliently biased toward an offset configuration relative to the longitudinal shaft axis, and (iii) an electrode disposed at the distal tip, wherein the electrode is operable to deliver RF energy to tissue for ablating the tissue, wherein the needle is translatable relative to the outer tube between a proximal retracted position in which the distal tip is housed within the outer tube, and a distal extended position in which the distal tip is exposed from the outer tube, wherein the distal tip is configured to resiliently transition from a first configuration to the offset configuration in response to distal extension of the distal tip from the outer tube.

Example 17

The surgical instrument of Example 16, wherein the distal tip is configured to extend coaxially with the longitudinal shaft axis when in the first configuration.

Example 18

The surgical instrument of any of Examples 16 through 17, wherein the offset configuration comprises at least one of a curved configuration or an angled configuration relative to the longitudinal shaft axis.

Example 19

A method of ablating a posterior nasal nerve of a patient with an RF ablation instrument, wherein the RF ablation instrument includes an outer tube and a needle slidably disposed within the outer tube and having a distal needle tip with an electrode, the method comprising: (a) inserting a distal end of the RF ablation instrument into a nasal cavity of the patient while the distal needle tip remains retracted within the outer tube; (b) positioning the distal end of the RF ablation instrument at a portion of the nasal wall that overlies the posterior nasal nerve; (c) actuating the needle distally to expose the distal needle tip from the outer tube; (d) piercing the nasal wall with the exposed distal needle tip to place the electrode in electrical contact with the posterior nasal nerve; and (e) energizing the electrode with RF energy to thereby ablate a portion of the posterior nasal nerve with the RF energy.

Example 20

The method of Example 19, wherein the needle includes a lumen that opens to the distal needle tip, wherein the method further comprises delivering a fluid into the nasal wall through the distal needle tip while energizing the electrode with RF energy.

V. MISCELLANEOUS

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, Calif. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013, the disclosure of which is incorporated by reference herein; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, embodiments, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of using a surgical instrument, the surgical instrument comprising:
   (a) an outer tube configured to be gripped by a user; and
   (b) a needle slidably disposed within the outer tube, wherein the needle comprises:
      (i) a needle lumen,
      (ii) a distal needle tip configured to pierce tissue, wherein the needle lumen opens to the distal needle tip such that the distal needle tip is configured to deliver fluid from the needle lumen to tissue, and
      (iii) an electrode disposed at the distal needle tip, wherein the electrode is operable to deliver RF energy to tissue for ablating the tissue,
   wherein the needle is translatable relative to the outer tube between a proximal retracted position in which the distal needle tip is housed coaxially within the outer tube, and a distal extended position in which the distal needle tip is exposed from the outer tube and configured to pierce tissue,
   wherein the needle further comprises a needle shaft that extends longitudinally along a shaft axis, wherein the distal needle tip extends distally from the needle shaft and is resiliently biased toward an offset configuration in which the distal needle tip is non-coaxial with the shaft axis,
   wherein the distal needle tip is configured to remain straight when in the proximal retracted position,
   the method comprising:
   advancing the needle distally from the proximal retracted position to a distal position, the needle tip being positioned in a posterior nasal nerve in the distal position, the needle tip transitioning from the straight configuration to the offset configuration as the needle is advanced distally from the proximal retracted position to the distal position.

2. The method of claim 1, wherein the electrode is configured to deliver monopolar RF energy to tissue when the needle is in the distal extended position.

3. The method of claim 1, wherein the distal needle tip comprises an electrically conductive material that defines the electrode.

4. The method of claim 1, further comprising an electrically insulative layer positioned between an outer surface of the needle and an inner surface of the outer tube.

5. The method of claim 4, wherein the electrically insulative layer is secured to the needle such that a distal end of the electrically insulative layer terminates proximally of the distal needle tip.

6. The method of claim 1, wherein a proximal end of the needle is configured to couple with a fluid source, wherein the needle lumen is configured to communicate fluid from the fluid source to tissue through the distal needle tip.

7. The method of claim 1, wherein an opening of the distal needle tip is oriented away from the shaft axis in the offset configuration.

8. The method of claim 1, wherein the offset configuration comprises at least one of a curved configuration or an angled configuration.

9. The method of claim 1, wherein the needle further comprises an electrical connector, wherein the electrical connector is configured to electrically couple with an RF energy source.

10. The method of claim 1, wherein the needle further comprises a lateral projection, wherein the outer tube includes a longitudinal slot that slidably receives the lateral projection, wherein the lateral projection is exposed through the longitudinal slot such that the lateral projection is configured to be engaged by a user to actuate the needle relative to the outer tube.

11. The method of claim 1, wherein the needle further comprises:
   (i) a first projection extending laterally from a first portion of the needle, and
   (ii) a second projection extending laterally from a second portion of the needle,
   wherein the outer tube comprises:
   (i) a first longitudinal slot configured to slidably receive the first projection therethrough, and
   (ii) a second longitudinal slot configured to slidably receive the second projection therethrough.

12. The method of claim 11, wherein the first projection comprises an actuator tab, wherein the second projection comprises an electrical connector.

13. The method of claim 11, wherein the first projection and the second projection are both coupled to the needle shaft and wherein the second projection is slidable dependent on a position of the first projection.

14. The method of claim 1, wherein the outer tube and the needle are configured to extend coaxially along a central axis of the surgical instrument when the needle is in the proximal retracted position.

15. A method of using a surgical system the perform the method of claim 1, the surgical system comprising:
   (a) an RF energy source operatively coupled with the electrode of the needle;
   (b) a fluid source operatively coupled with the needle lumen; and
   (c) a ground pad operatively coupled with the RF energy source,
   wherein the surgical instrument is operable to energize the electrode with RF energy from the RF energy source while dispensing fluid from the fluid source through the distal needle tip,
   wherein the electrode is configured to cooperate with the ground pad to deliver monopolar RF energy to tissue for ablating the tissue,
   the method further comprising:
   activating the RF energy source and dispensing fluid from the fluid source through the distal needle tip while the needle is in the distal position.

16. A method of using a surgical instrument, the surgical instrument comprising:
   (a) an outer tube; and
   (b) a needle slidably disposed within the outer tube, wherein the needle comprises:
      (i) a shaft defining a longitudinal shaft axis,
      (ii) a distal tip configured to pierce tissue, wherein the distal tip is resiliently biased toward an offset configuration relative to the longitudinal shaft axis, and
      (iii) an electrode disposed at the distal tip, wherein the electrode is operable to deliver RF energy to tissue for ablating the tissue, wherein the needle is translatable relative to the outer tube between a proximal retracted position in which the distal tip is housed within the outer tube, and a distal extended position in which the distal tip is exposed from the outer tube, wherein the distal tip is configured to resiliently transition from a straight configuration to the offset configuration in response to distal extension of the distal tip from the outer tube, the method comprising:

advancing the needle distally from the proximal retracted position to the distal extended position, the needle tip being positioned in a posterior nasal nerve in the distal extended position, the needle tip transitioning from the straight configuration to the offset configuration as the needle is advanced distally from the proximal retracted position to the distal extended position.

17. The method of claim 16, wherein the distal tip is configured to extend coaxially with the longitudinal shaft axis when in the straight configuration.

18. The method of claim 16, wherein the offset configuration comprises at least one of a curved configuration or an angled configuration relative to the longitudinal shaft axis.

19. A method of ablating a posterior nasal nerve of a patient with an RF ablation instrument, wherein the RF ablation instrument includes an outer tube and a needle slidably disposed within the outer tube and having a distal needle tip with an electrode, wherein the needle defines a longitudinal shaft axis and has a resilient bias urging the distal needle tip toward an offset configuration relative to the longitudinal shaft axis, the method comprising:

(a) inserting a distal end of the RF ablation instrument into a nasal cavity of the patient while the distal needle tip remains retracted within the outer tube, the nasal cavity having a nasal wall;

(b) positioning the distal end of the RF ablation instrument at a portion of the nasal wall that overlies the posterior nasal nerve;

(c) actuating the needle distally to expose the distal needle tip from the outer tube, the exposed distal needle tip being transitioned to the offset configuration by the resilient bias;

(d) piercing the nasal wall with the exposed distal needle tip to place the electrode in electrical contact with the posterior nasal nerve; and (e) energizing the electrode with RF energy to thereby ablate a portion of the posterior nasal nerve with the RF energy.

20. The method of claim 19, wherein the needle includes a lumen that opens to the distal needle tip, wherein the method further comprises delivering a fluid into the nasal wall through the distal needle tip while energizing the electrode with RF energy.

* * * * *